United States Patent
Mayer et al.

(10) Patent No.: US 7,993,587 B2
(45) Date of Patent: Aug. 9, 2011

(54) HUMIDITY CONTROL SYSTEM FOR THE SENSING CELL OF AN ANALYTE PERMEATION TESTING INSTRUMENT

(75) Inventors: Daniel W. Mayer, Wyoming, MN (US); Stephen D. Tuomela, Ramsey, MN (US)

(73) Assignee: Mocon, Inc., Minneapolis, MN (US)

( * ) Notice: Subject to any disclaimer, the term of this patent is extended or adjusted under 35 U.S.C. 154(b) by 750 days.

(21) Appl. No.: 12/114,515

(22) Filed: May 2, 2008

(65) Prior Publication Data
US 2010/0054998 A1    Mar. 4, 2010

(51) Int. Cl.
*G01N 7/00* (2006.01)
(52) U.S. Cl. .......... 422/83; 436/43; 236/44 R; 236/44 C
(58) Field of Classification Search ............... 422/83; 436/43; 236/44 R, 44 C
See application file for complete search history.

(56) References Cited

U.S. PATENT DOCUMENTS

| | | |
|---|---|---|
| 3,531,916 A | 10/1970 | Kulperger et al. |
| 5,107,696 A | 4/1992 | Mayer et al. |
| 5,159,829 A | 11/1992 | Mayer et al. |
| 5,173,258 A | 12/1992 | Childers |
| 5,824,918 A | 10/1998 | Zuk |
| 5,988,003 A | 11/1999 | Zuk |
| 6,616,330 B2 | 9/2003 | Nakamura et al. |
| 7,478,760 B2 * | 1/2009 | Beatty et al. ............ 236/44 A |
| 2004/0058437 A1 * | 3/2004 | Rodgers et al. ........... 435/297.1 |
| 2004/0099140 A1 * | 5/2004 | Hesse et al. ............. 96/8 |
| 2007/0023536 A1 | 2/2007 | Baston |

* cited by examiner

*Primary Examiner* — Brian J Sines
*(74) Attorney, Agent, or Firm* — Sherrill Law Offices PLLC

(57) ABSTRACT

A humidity control system for an analyte permeation testing instrument. The system includes (i) an analyte permeation testing instrument, (ii) a sensor for sensing a target analyte, (iii) a humidity control chamber, and (iv) a selectively permeable membrane permeable to water vapor and impermeable to the target analyte. The analyte permeation testing instrument defines a testing chamber operable for engaging a test film such that the testing chamber is sealingly separated by the test film into a first cell and a second cell throughout a permeation testing period. The sensor is placed in fluid communication with the first cell. The humidity control chamber is positioned adjacent the first cell and in fluid communication with both a source of gas having a known humidity and the first cell, with the selectively permeable membrane sealingly separating the humidity control chamber from the first cell.

12 Claims, 19 Drawing Sheets

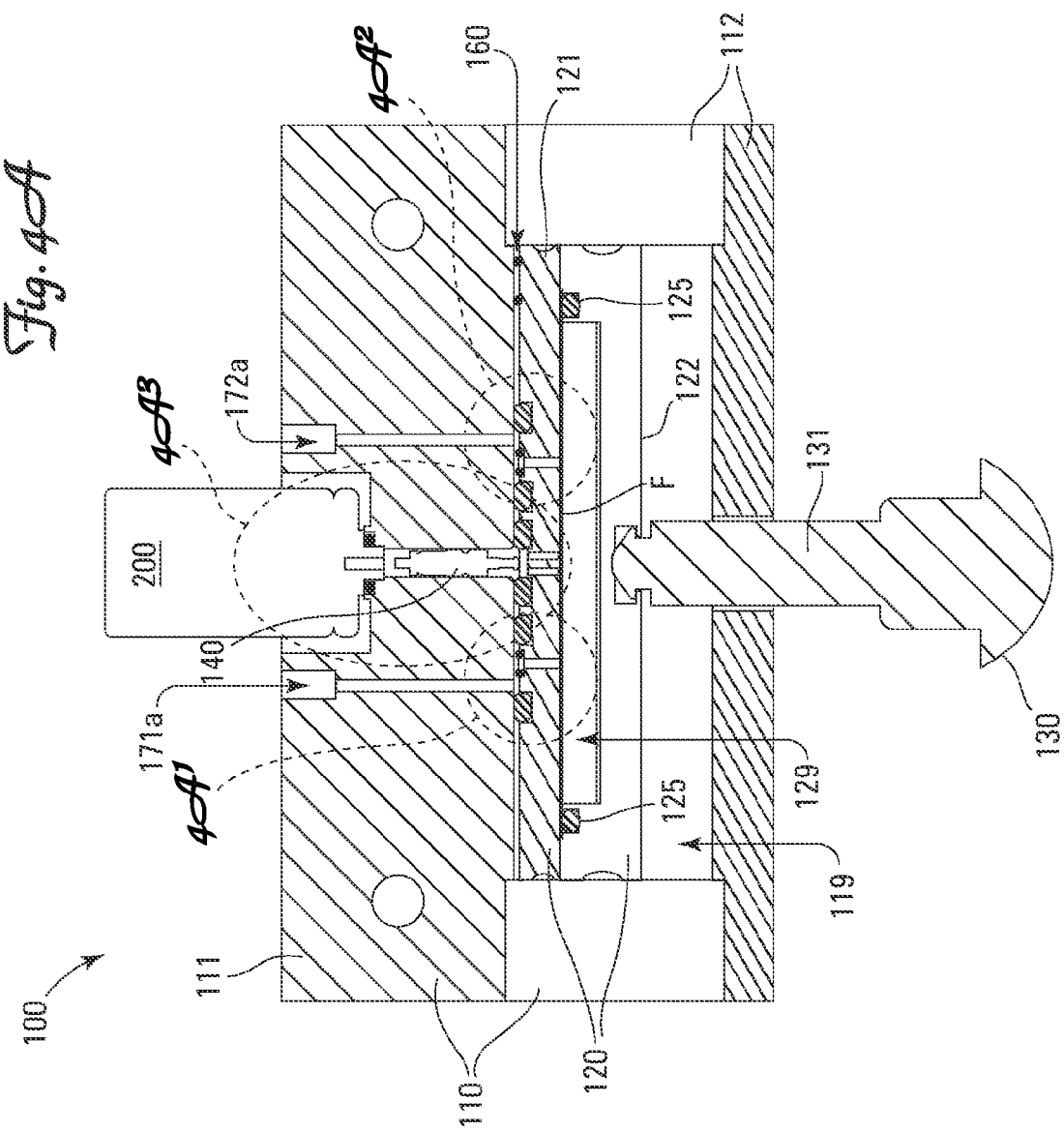

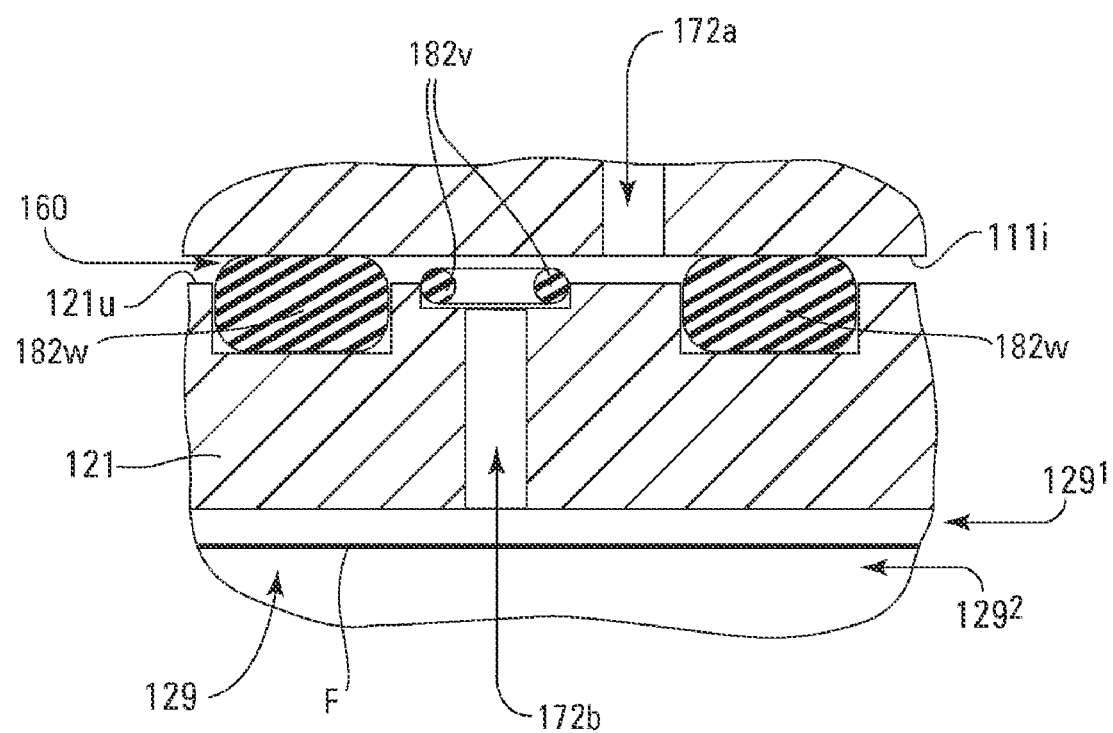
Fig. 4A²

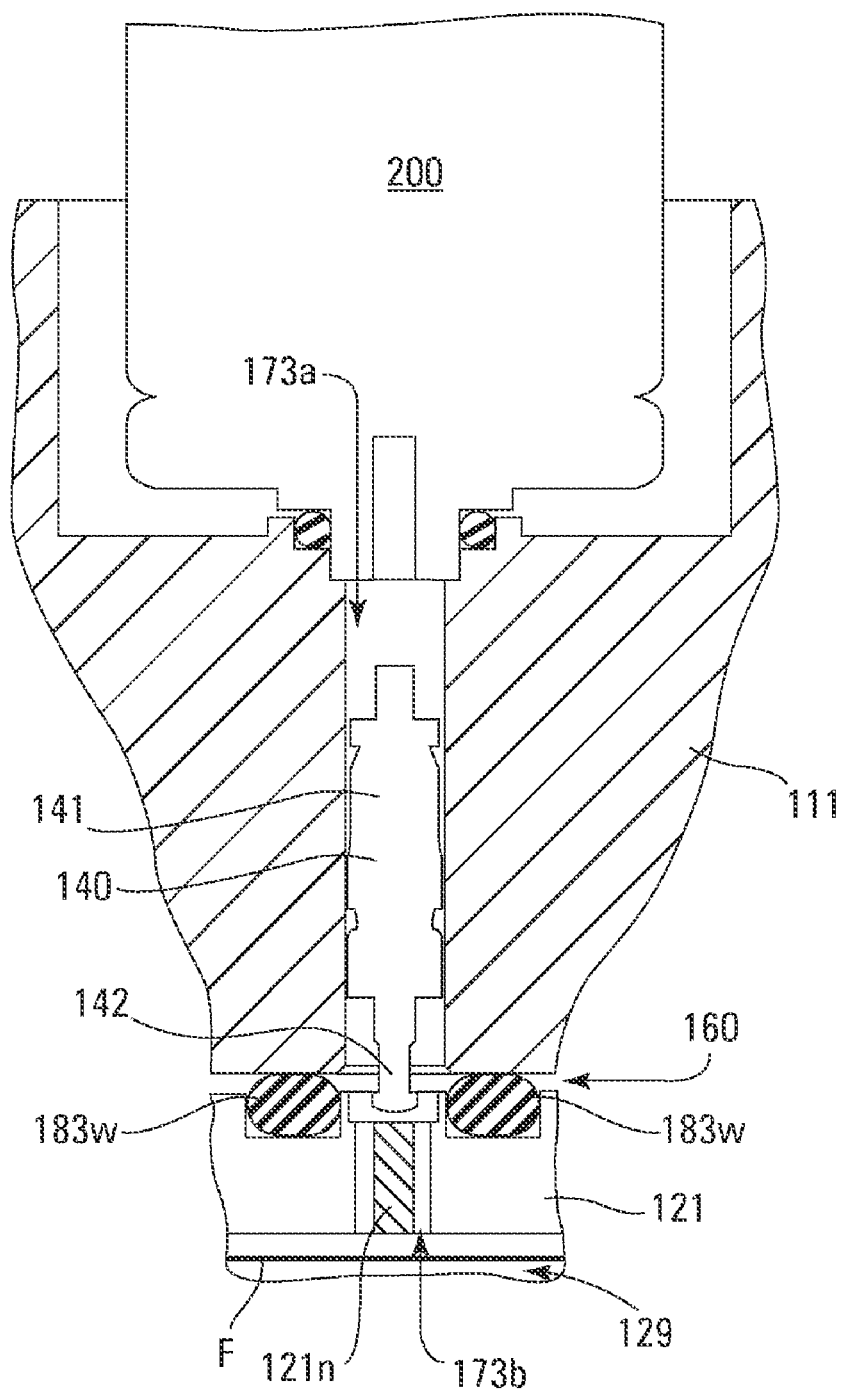
Fig. 4A³

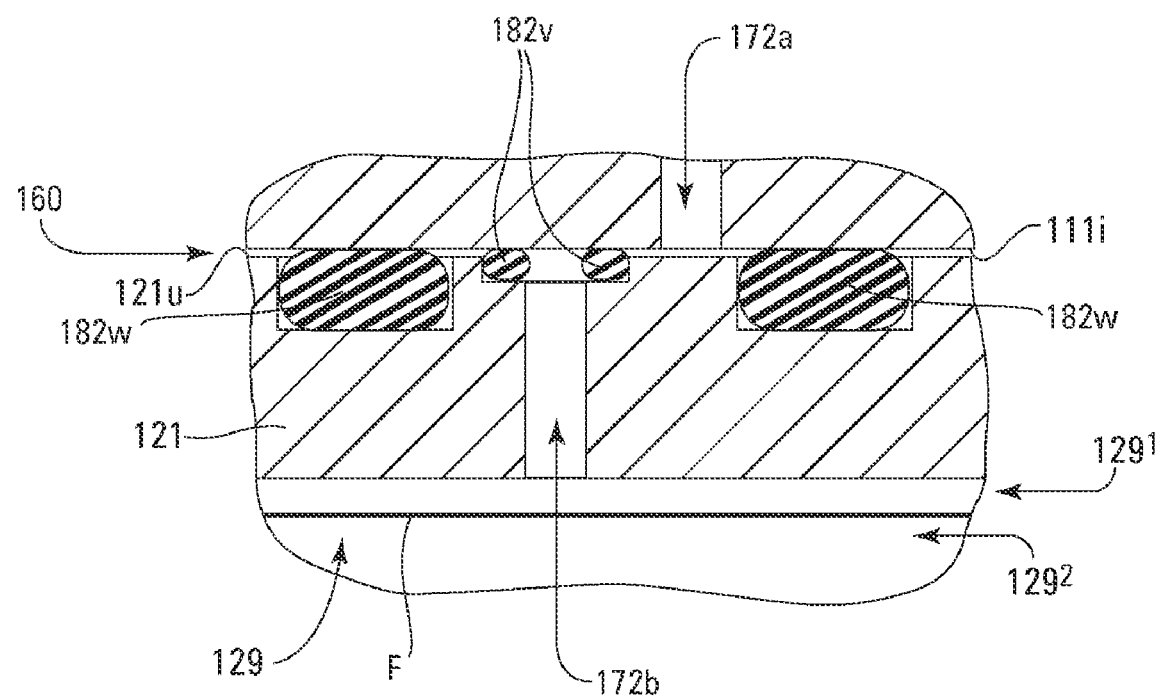
Fig. 4B²

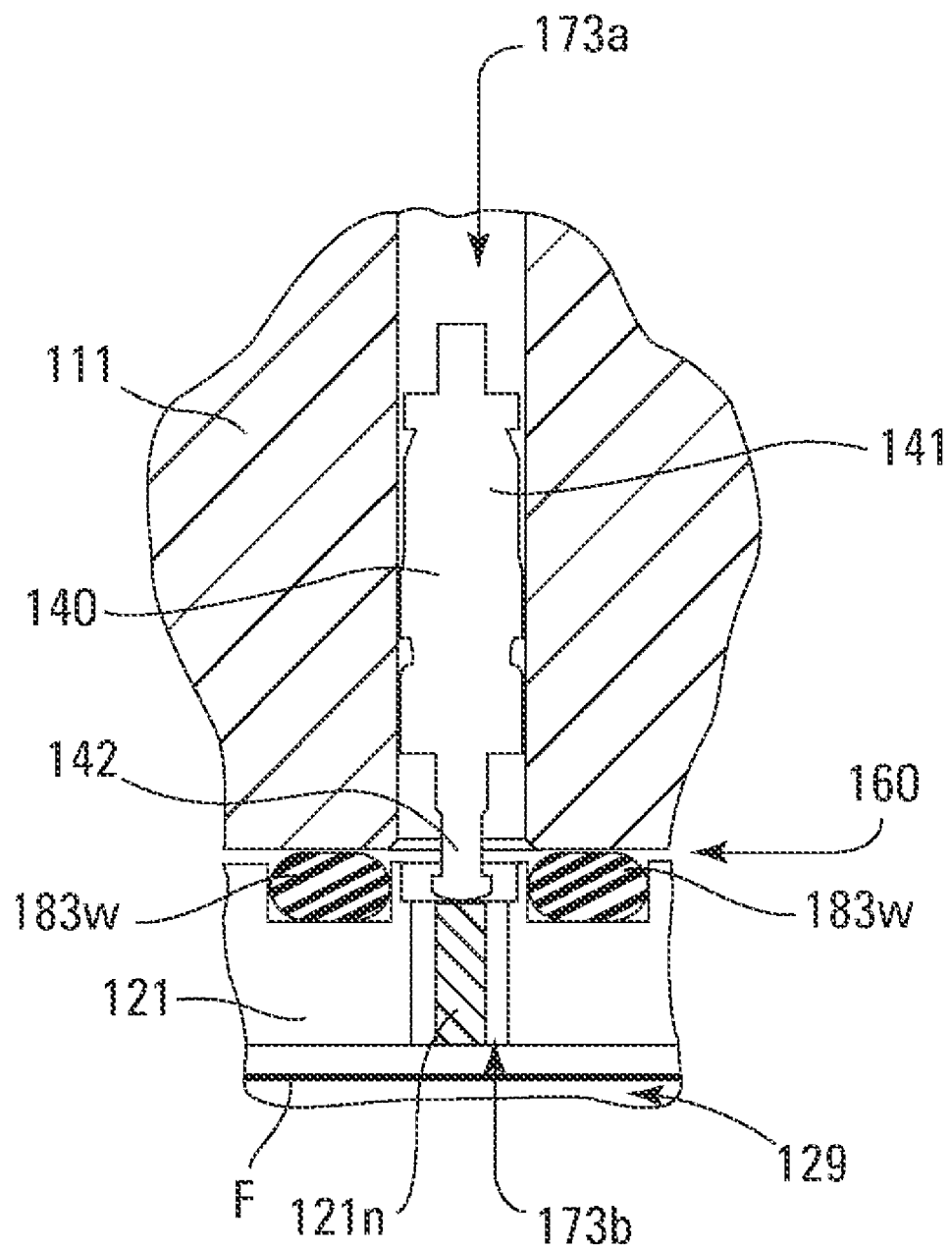
Fig. 4B³

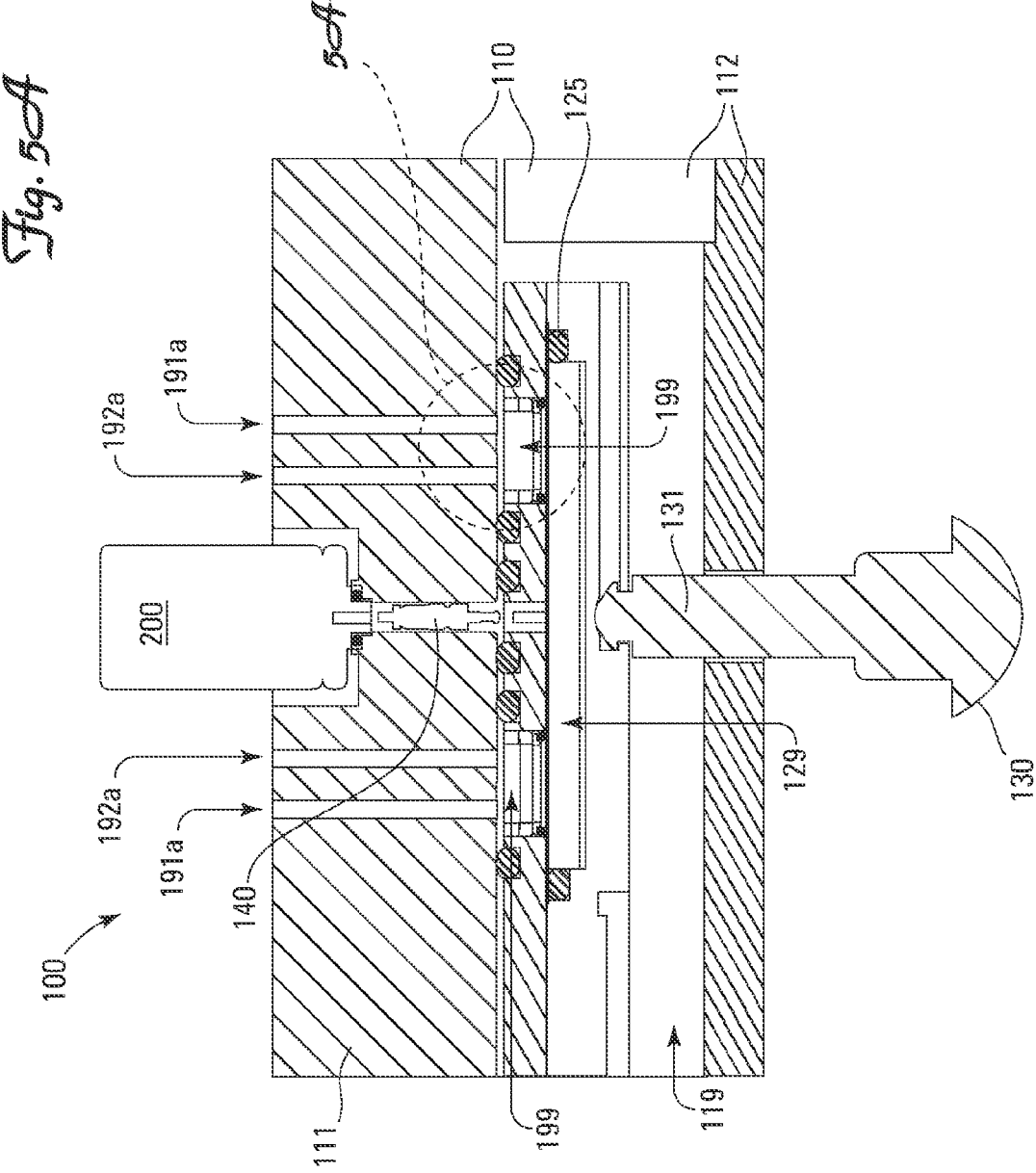

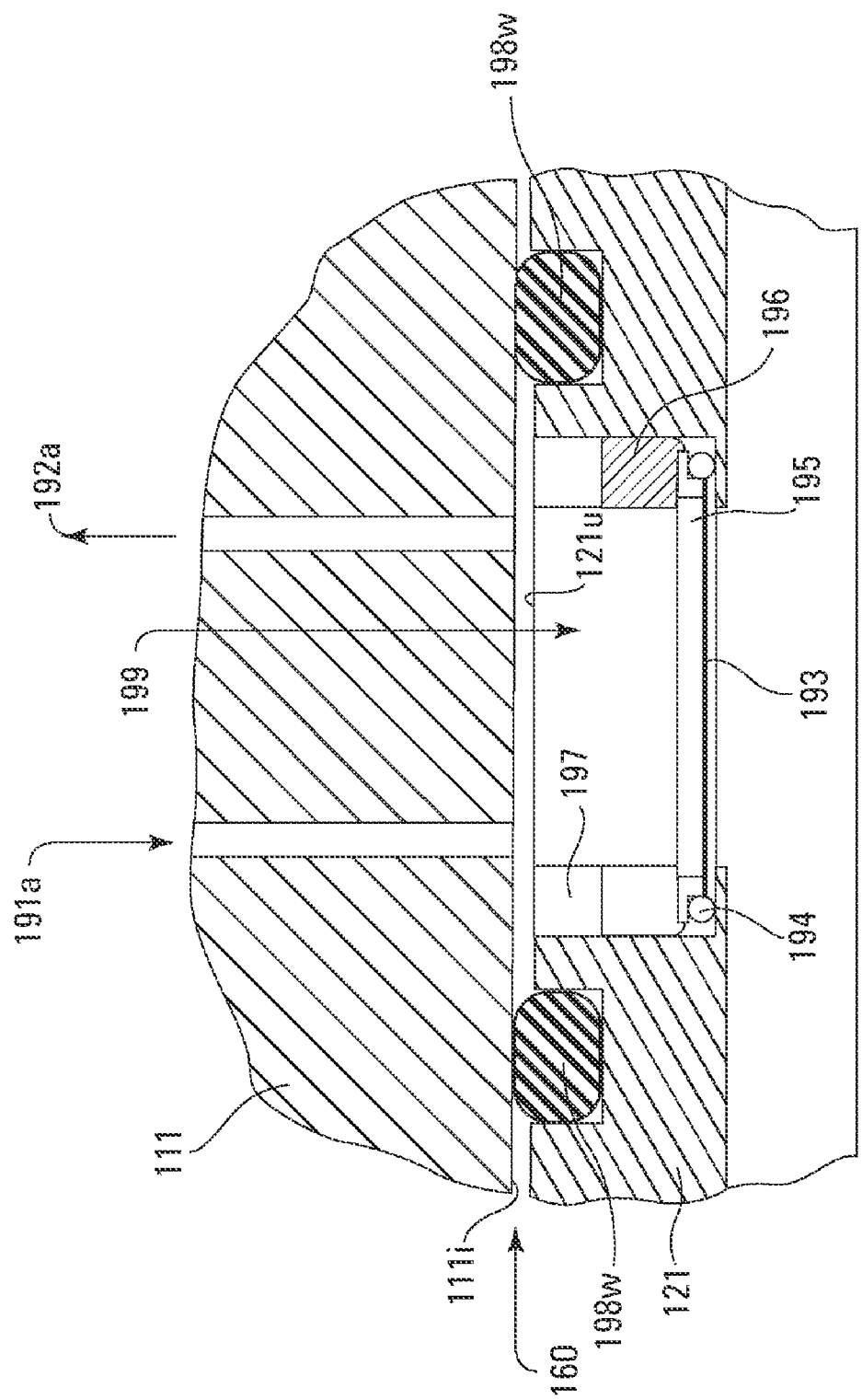

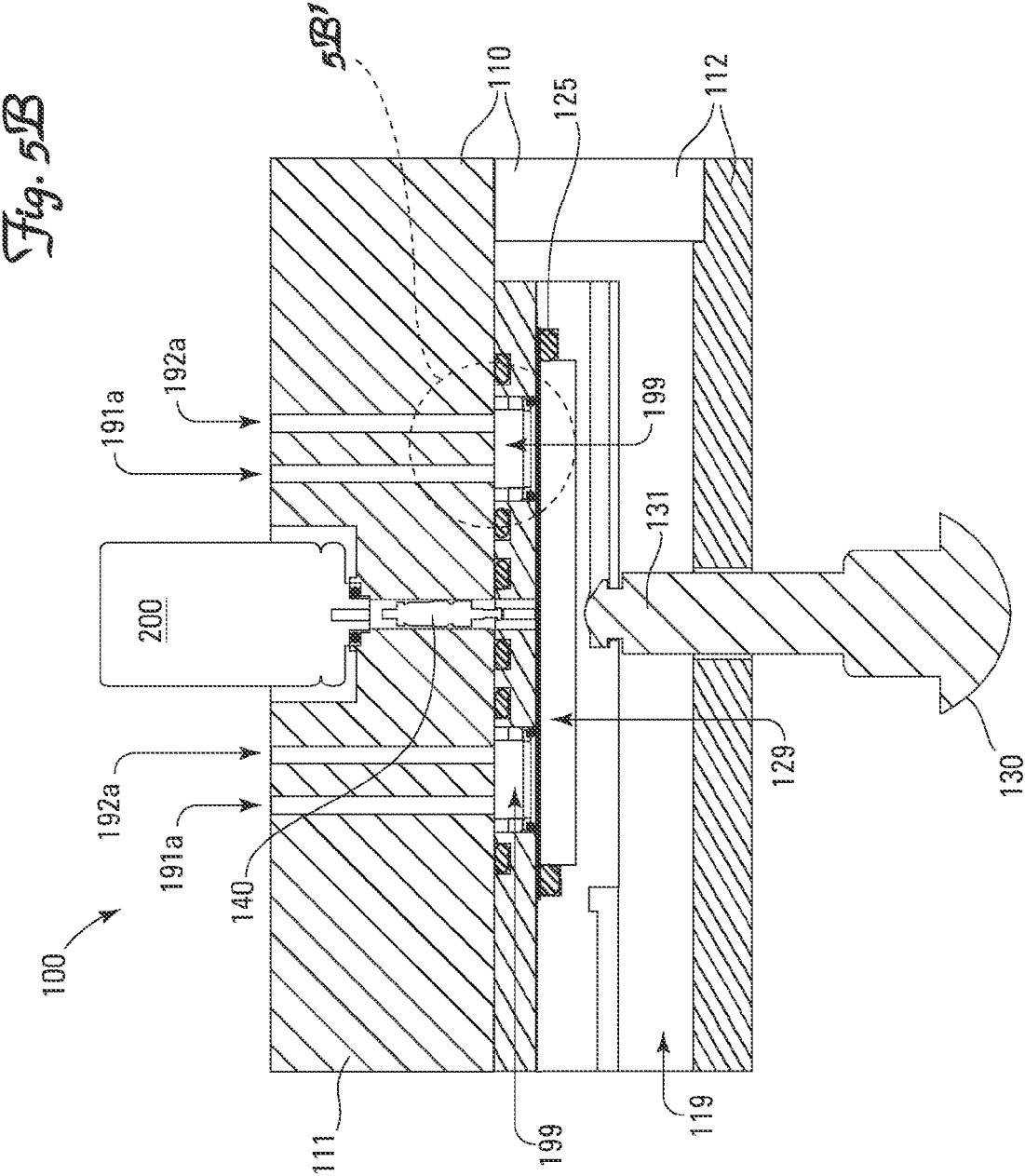

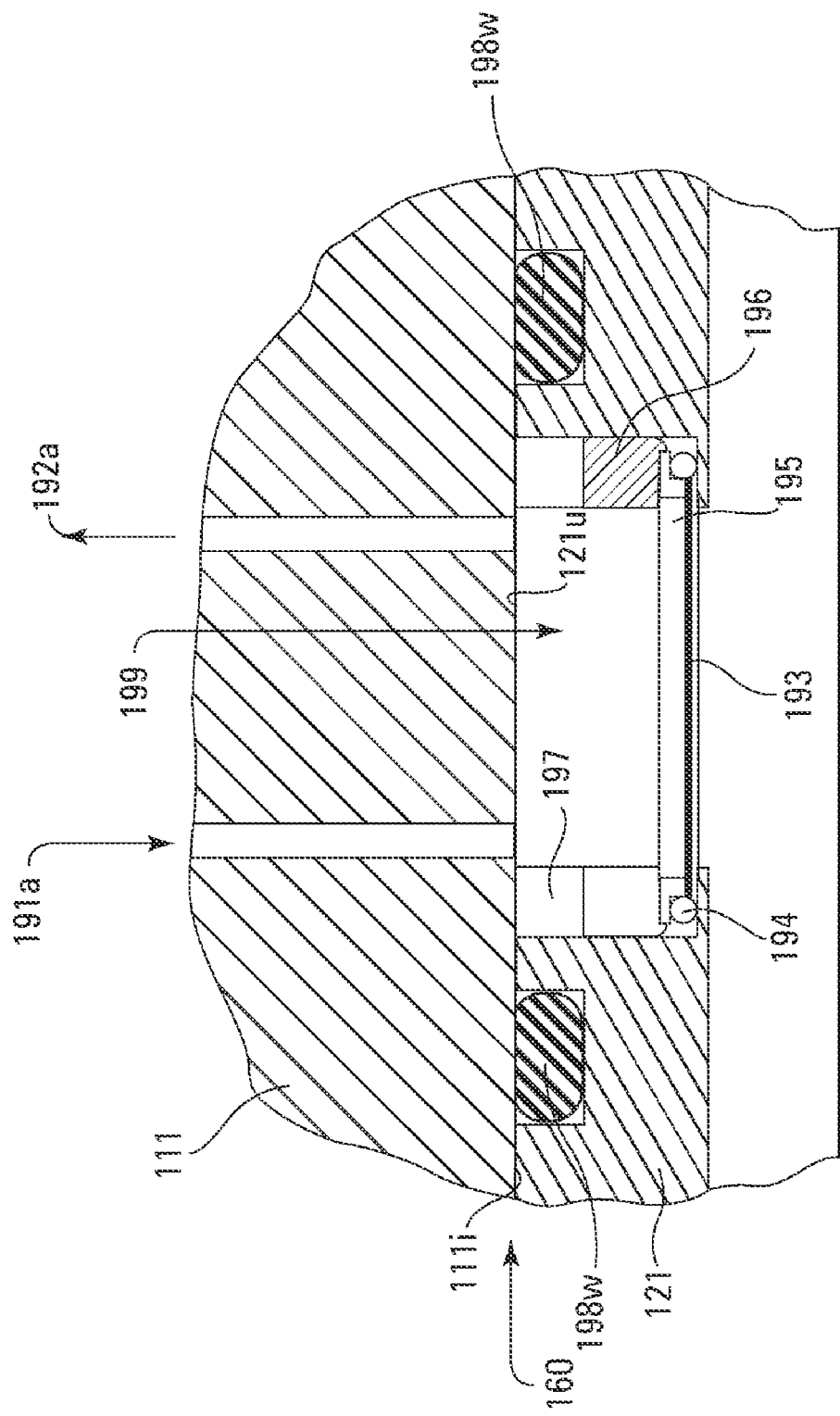

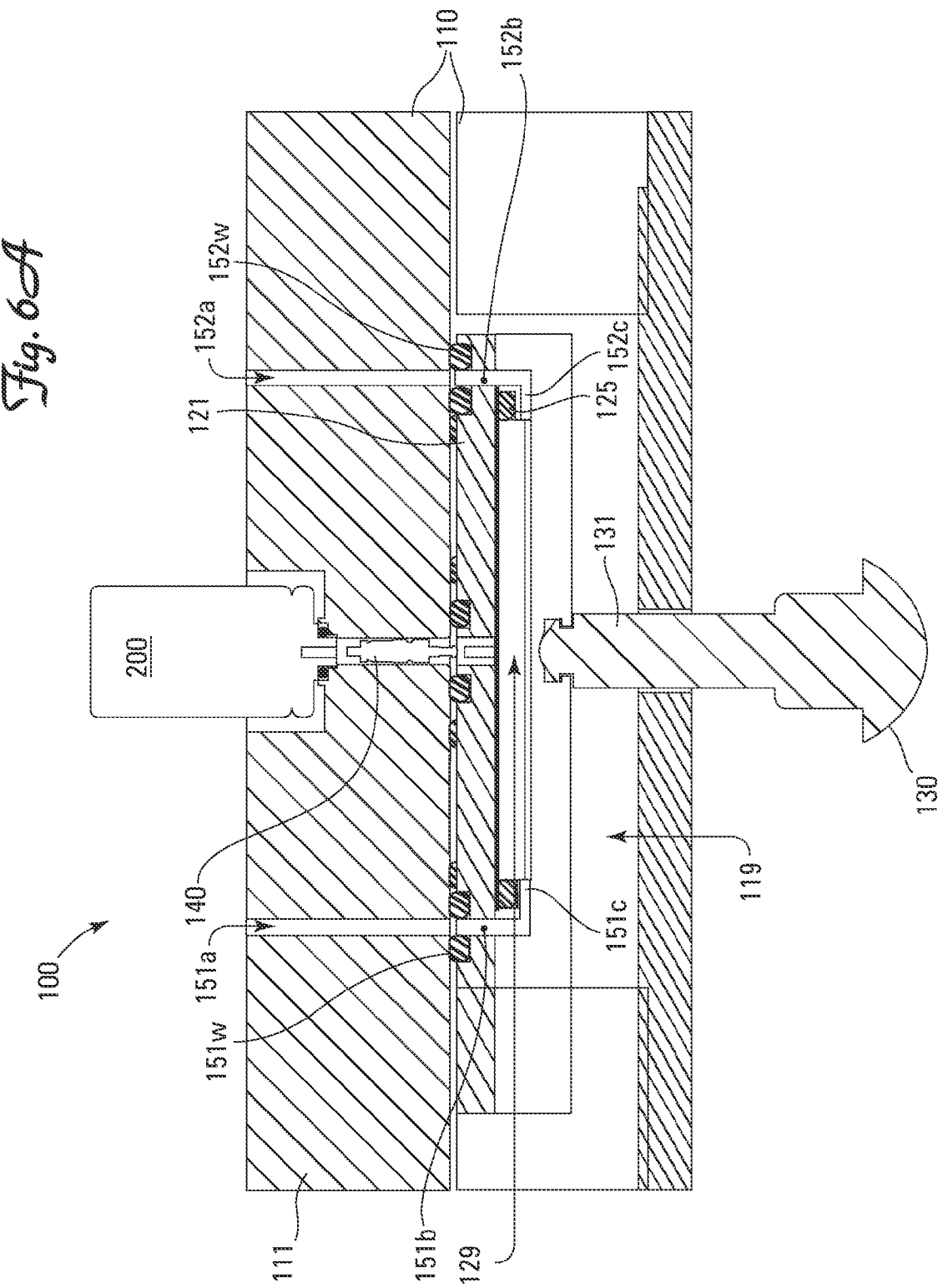

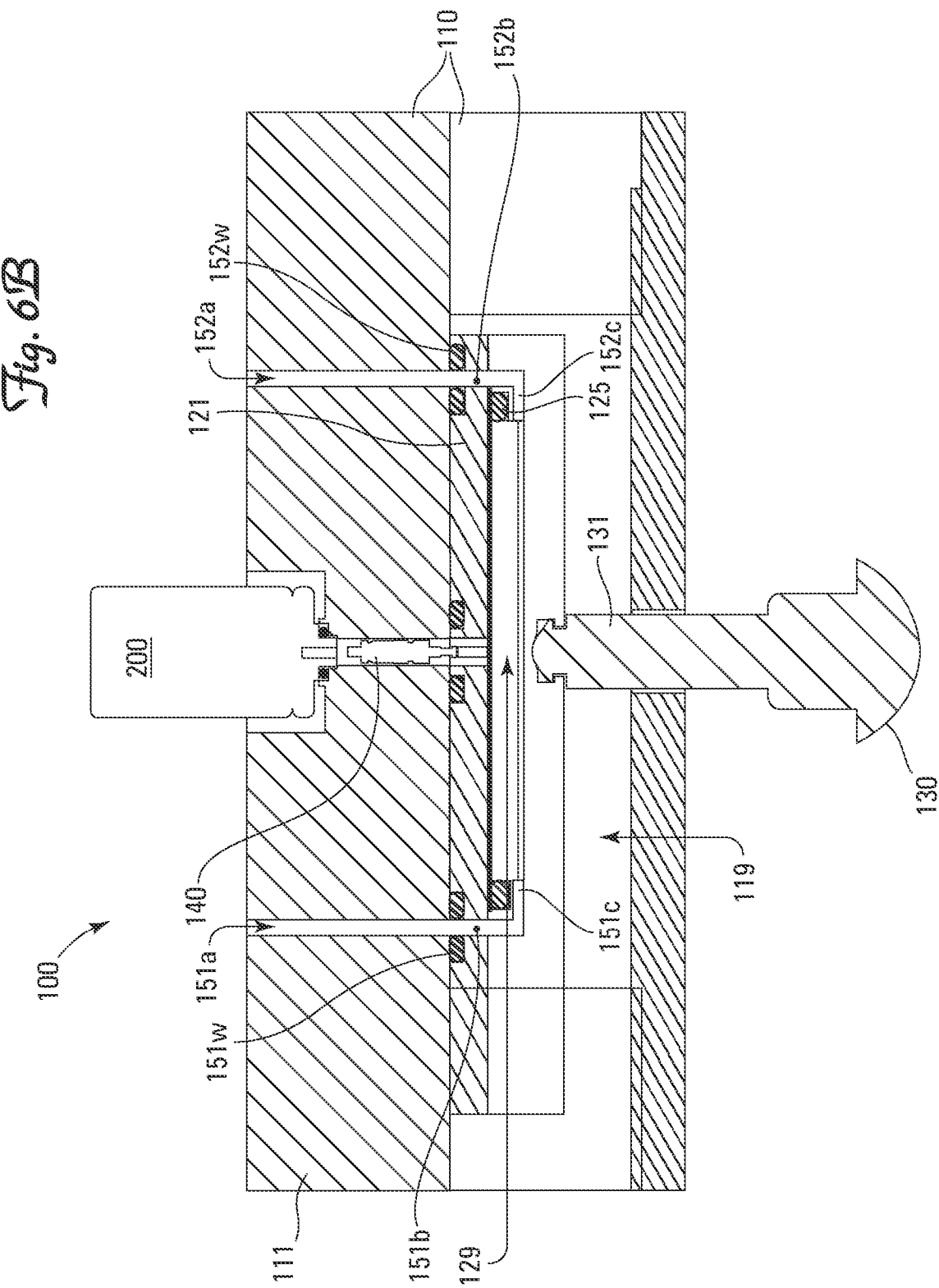

HUMIDITY CONTROL SYSTEM FOR THE SENSING CELL OF AN ANALYTE PERMEATION TESTING INSTRUMENT

BACKGROUND

Permeation instruments are used to measure the transmission rate of a target analyte, such as oxygen, carbon dioxide or water vapor, through a film of interest. Typical films subjected to permeation testing are polymeric packaging films such as those constructed from low density polyethylene (LDPE), high density polyethylene (HDPE), oriented polypropylene (OPP), polyethylene terephthalate (PET), polyvinylidene chloride (PVTDC), etc. Typically, the film to be tested is positioned within a test chamber to sealing separate the chamber into first and second cells. The first cell (commonly referenced as the sensing cell) is flushed with an inert gas to remove any target analyte from the cell and the second cell (commonly referenced as the analyte cell) filled with a gas containing a known concentration of the target analyte. A sensor for the target analyte detects the presence of target analyte that has migrated into the sensing cell from the analyte cell through the film.

Permeation instruments typically employ a flow-through method or an accumulation method for sensing the presence of target analyte in the sensing cell. Briefly, the flow-through method uses an inert flushing gas to continuously pick up any target analyte that has migrated into the sensing cell and deliver it to a remote sensor. The accumulation method allows target analyte to build up in the sensing cell for an accumulation period, with the sensor either positioned within the sensing cell or the sensing cell flushed with a flushing gas after the accumulation period for delivery of accumulated target analyte to a remote sensor.

The flow through method allows virtually all sensor types to be used, but are expensive and complex systems. The accumulation method, while permitting the use of less sensitive inexpensive sensors to accurately measure permeation of a target analyte through a film even at very low transmission rates, suffers from significantly longer test times.

Electrochemical sensors are generally preferred for use in permeation instruments as they provide a number of advantages, including (i) extreme accuracy, (ii) ultra-high sensitivity to analyte, (iii) high specificity for a single analyte, (iv) lack of temperature sensitivity, (v) lack of pressure sensitivity, (vi) minimal sensitivity to flow, and (vii) low cost.

Unfortunately, the permeation characteristics of most films are sensitive to humidity and most electrochemical sensors are wet sensors (i.e., the electrolyte is an aqueous solution) that can change the humidity within the sensing cell. Hence, in order to ensure consistent and accurate test results, the humidity within the sensing cell must be controlled.

The humidity within the sensing cell can be controlled for those systems employing the flow through method by controlling the humidity of the inert flushing gas flowing into the sensing cell. Unfortunately, this technique does not work for systems employing the accumulation method as the sensing cell is sealed to fluid flow during testing.

Accordingly, a substantial need exists for a system and method for controlling the humidity within the sensing cell of an analyte permeation testing instrument when the sensing cell is sealed to fluid flow during testing.

SUMMARY OF THE INVENTION

The invention is directed to a humidity control system for an analyte permeation testing instrument. The system includes (i) an analyte permeation testing instrument, (ii) a sensor for sensing a target analyte, (iii) a humidity control chamber, and (iv) a selectively permeable membrane permeable to water vapor and impermeable to the target analyte. The analyte permeation testing instrument defines a testing chamber operable for engaging a test film such that the testing chamber is sealingly separated by the test film into a first cell and a second cell throughout a permeation testing period. The sensor is placed in fluid communication with the first cell. The humidity control chamber is positioned adjacent the first cell and in fluid communication with both a source of gas having a known humidity and the first cell, with the selectively permeable membrane sealingly separating the humidity control chamber from the first cell.

Figure 4A:
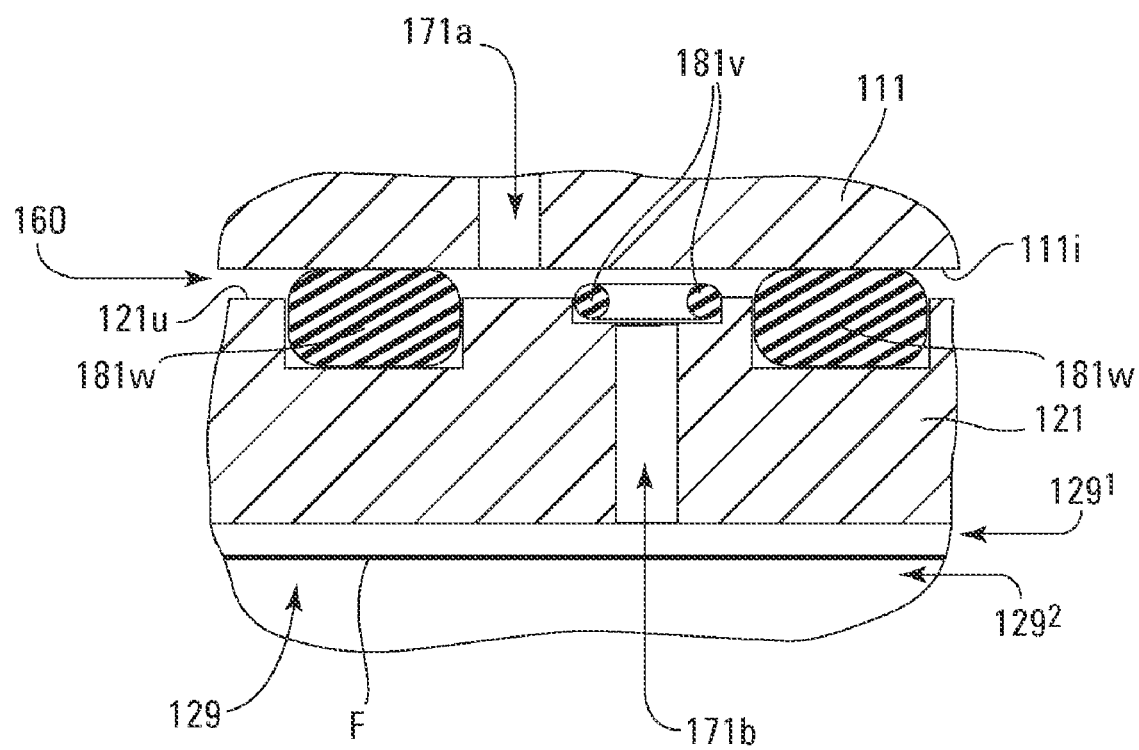
FIG. 4A is a cross-sectional side view of the measurement unit shown in FIG. 3 taken along line 4-4 with the upper mounting plate in the open position spaced a distance away from the upper portion of the housing.

FIG. $4A^1$ is an enlarged cross-sectional side view of the encircled inlet area of the gap in the measurement unit shown in FIG. 4A.

FIG. $4A^2$ is an enlarged cross-sectional side view of the encircled outlet area of the gap in the measurement unit shown in FIG. 4A.

FIG. $4A^3$ is an enlarged cross-sectional side view of the encircled sensor passageway area of the gap in the measurement unit shown in FIG. 4A.

Figure 3:
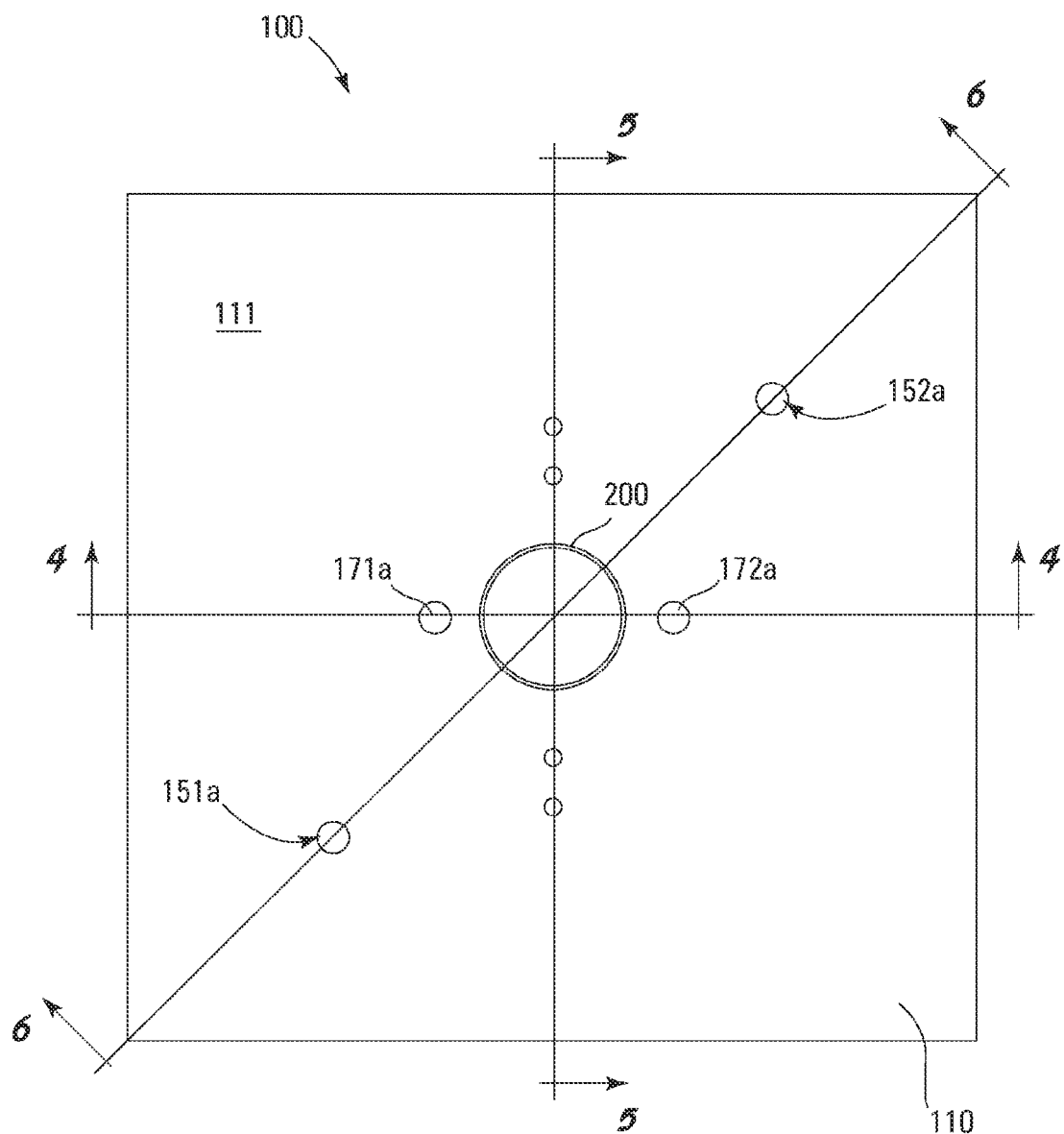
FIG. 3 is a top view of the measurement unit component of the testing system shown in FIG. 2.
Figure 4B:
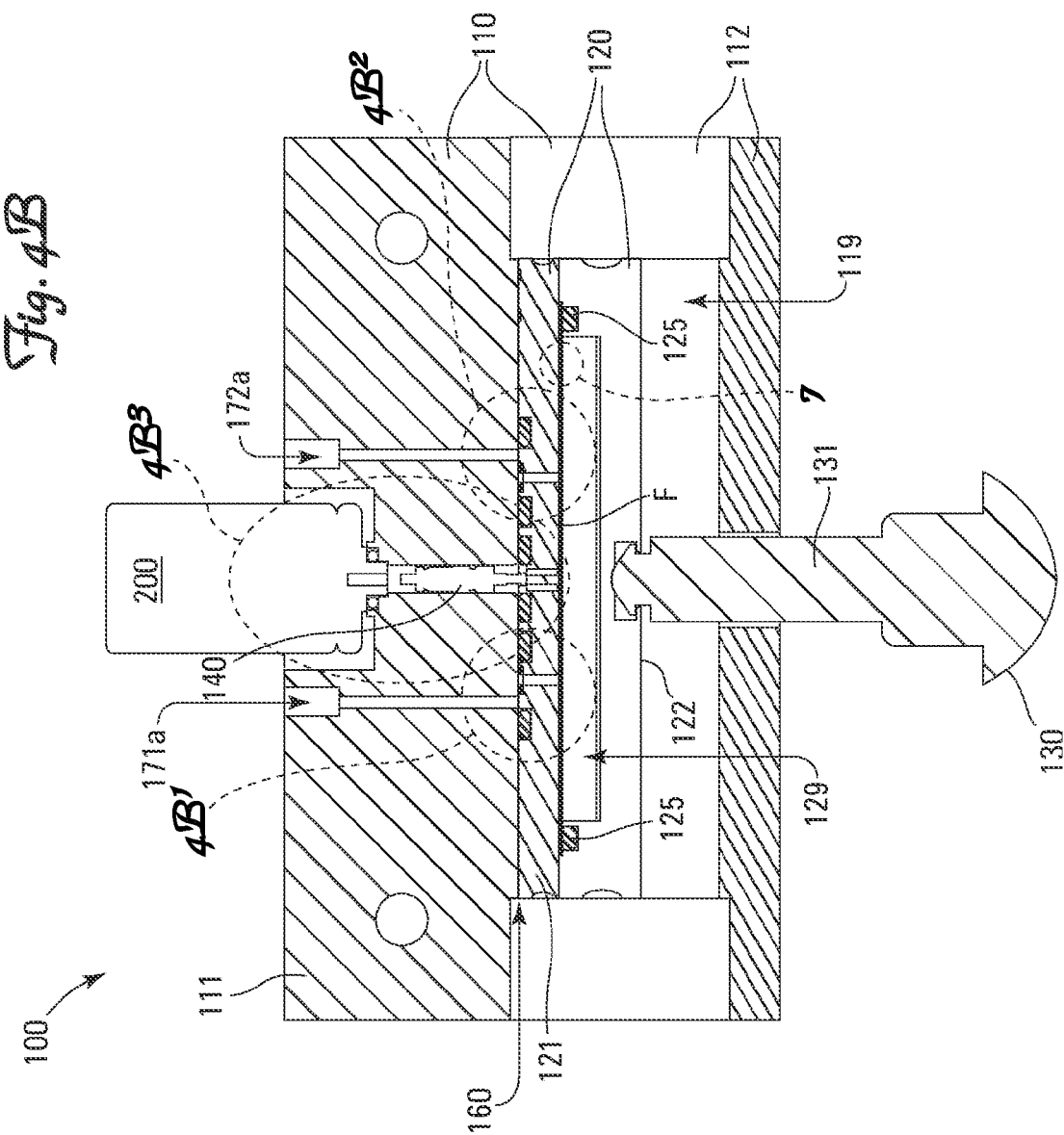

FIG. 4B is a cross-sectional side view of the measurement unit shown in FIG. 3 taken along line 4-4 with the upper mounting plate in the closed position immediately adjacent the upper portion of the housing.

FIG. $4B^1$ is an enlarged cross-sectional side view of the encircled inlet area of the gap in the measurement unit shown in FIG. 4B.

FIG. $4B^2$ is an enlarged cross-sectional side view of the encircled outlet area of the gap in the measurement unit shown in FIG. 4B.

FIG. $4B^3$ is an enlarged cross-sectional side view of the encircled sensor passageway area of the gap in the measurement unit shown in FIG. 4B.

FIG. 5A is a cross-sectional side view of the measurement unit shown in FIG. 3 taken along line 5-5 with the upper mounting plate in the open position spaced a distance away from the upper portion of the housing.

FIG. $5A^1$ is an enlarged cross-sectional side view of the encircled humidity control window in the measurement unit shown in FIG. 5A.

FIG. 5B is a cross-sectional side view of the measurement unit shown in FIG. 3 taken along line 5-5 with the upper mounting plate in the closed position immediately adjacent the upper portion of the housing.

FIG. $5B^1$ is an enlarged cross-sectional side view of the encircled humidity control window in the measurement unit shown in FIG. 5B.

FIG. 6A is a cross-sectional side view of the measurement unit shown in FIG. 3 taken along line 6-6 with the upper mounting plate in the open position spaced a distance away from the upper portion of the housing.

FIG. 6B is a cross-sectional side view of the measurement unit shown in FIG. 3 taken along line 6-6 with the upper mounting plate in the closed position spaced a distance away from the upper portion of the housing.

Figure 7:
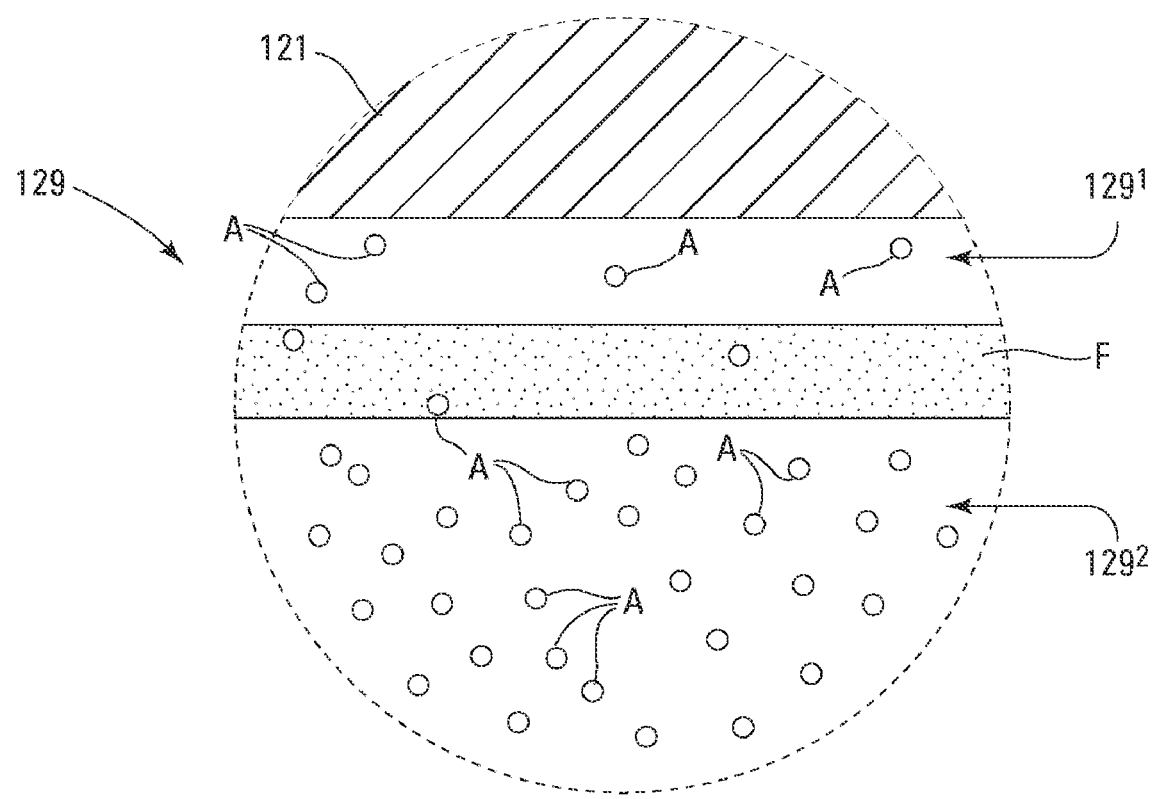

FIG. 7 is a grossly enlarged side view of the encircled portion of the testing chamber shown in FIG. 3 depicting individual molecules of an analyte of interest on each side of a test film being tested with the measurement unit shown in FIG. 4B.

Figure 8:
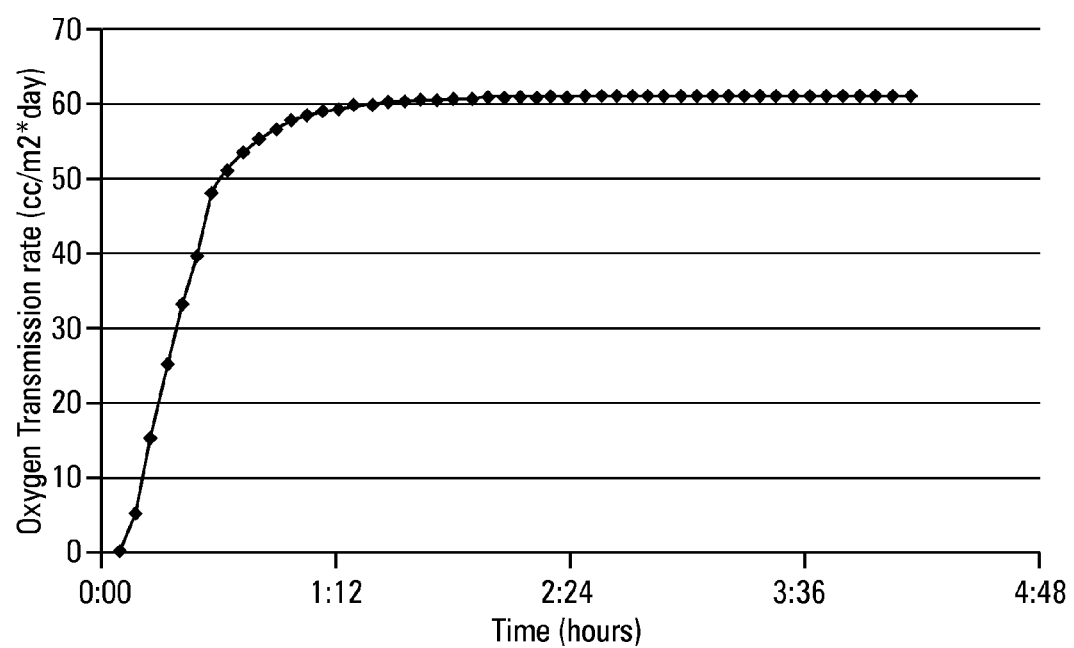

FIG. 8 is a graph of the $O_2$ transmission rate over time obtained from the permeation testing conducted in Example 1.

DETAILED DESCRIPTION OF A PREFERRED EMBODIMENT

Nomenclature

| | |
|---|---|
| 10 | Testing System |
| 21 | Source of Inert Gas |
| 22 | Source of Test Gas |
| 31a | Inlet Shutoff Valve for Source of Inert Gas |
| 31b | Outlet Shutoff Valve for Source of Inert Gas |
| 32a | Inlet Shutoff Valve for Source of Test Gas |
| 32b | Outlet Shutoff Valve for Source of Test Gas |
| 41a | Inlet Conduit for Directing Gas From the Source of Inert Gas Into the Upper Cell |
| 41b | Outlet Conduit for Venting Gas From the Upper Cell |
| 42a | Inlet Conduit for Directing Gas From the Source of Test Gas Into the Lower Cell |
| 42b | Outlet Conduit for Venting Gas From the Lower Cell |
| 50 | Computer or CPU |
| 60 | Monitor |
| 70 | Printer |
| 80 | Electrical Leads from the Sensor to the CPU |
| 100 | Measurement Unit |
| 110 | Housing |
| 111 | Upper Section of Housing |
| 111i | Lower Surface of Upper Section of Housing |
| 112 | Lower Section of Housing |
| 119 | Retention Chamber Defined by Housing |
| 120 | Mounting Plates |
| 121 | Upper Mounting Plate |
| 121u | Upper Surface of Upper Mounting Plate |
| 121n | Pin On Upper Mounting Plate |
| 122 | Lower Mounting Plate |
| 125 | O-ring Between Mounting Plates |
| 129 | Testing Chamber Defined by Mounting Plates |
| $129^1$ | Upper Cell of Testing Chamber |
| $129^2$ | Lower Cell of Testing Chamber |
| 130 | Actuator |
| 131 | Actuator Shaft |
| 140 | Valve for Passageway to Analyte Sensor |
| 141 | Valve Body |
| 142 | Valve Stem |
| 151a | Inlet Channel to Lower Cell Through Upper Section of Housing |
| 151b | Inlet Channel to Lower Cell Through Upper Mounting Plate |
| 151c | Inlet Channel to Lower Cell Through Lower Mounting Plate |
| 151w | Larger O-ring within Gap Encircling Inlet Passageways into the Lower Cell |
| 152a | Outlet Channel from Lower Cell Through Upper Section of Housing |
| 152b | Outlet Channel from Lower Cell Through Upper Mounting Plate |
| 152c | Outlet Channel from Lower Cell Through Lower Mounting Plate |
| 152w | Larger O-ring within Gap Encircling Outlet Passageways from the Lower Cell |
| 160 | Gap Between Upper Section of Housing and Upper Mounting Plate |
| 170 | Flow Control Channels and Passageways Through the Upper Section of the Housing and the Upper Mounting Plate |
| 171a | Inlet Channel to Gap Through Upper Section of Housing |
| 171b | Inlet Channel from Gap to Upper Cell Through Upper Mounting Plate |
| 172a | Outlet Channel from Gap Through Upper Section of Housing |
| 172b | Outlet Channel from Upper Cell to Gap Through Upper Mounting Plate |
| 173a | Passageway from Gap to Analyte Sensor Through Upper Section of Housing |
| 173b | Passageway from Upper Cell to Gap Through Upper Mounting Plate |
| 180 | O-Ring Seals within the Gap |
| 181v | Smaller O-ring within Gap Encircling Inlet Channel through Upper Mounting Plate |
| 181w | Larger O-ring within Gap Encircling Both Inlet Channels |
| 182v | Smaller O-ring within Gap Encircling Outlet Channel through Upper Mounting Plate |
| 182w | Larger O-ring within Gap Encircling Both Outlet Channels |
| 183w | Larger O-ring within Gap Encircling Passageways Leading to the Sensor |
| 190 | Humidity Control System |
| 191a | Inlet Channel to Humidity Control Chamber Through Upper Section of Housing |
| 192a | Outlet Channel from Humidity Control Chamber Through Upper Section of Housing |
| 193 | Selectively Permeable Film |
| 194 | O-ring |
| 195 | Washer |
| 196 | Inset Ring |
| 197 | Locking Ring |
| 198w | Larger O-ring within Gap Encircling Both Inlet and Outlet Channels for a Humidity Control Chamber |
| 199 | Humidity Control Chambers in the Upper Mounting Plate |
| 200 | Analyte Sensor |
| A | Analyte Molecules |
| F | Film Being Tested |
| x | Lateral Direction |
| y | Longitudinal Direction |
| z | Transverse Direction |

Description

Overview

Figure 1:
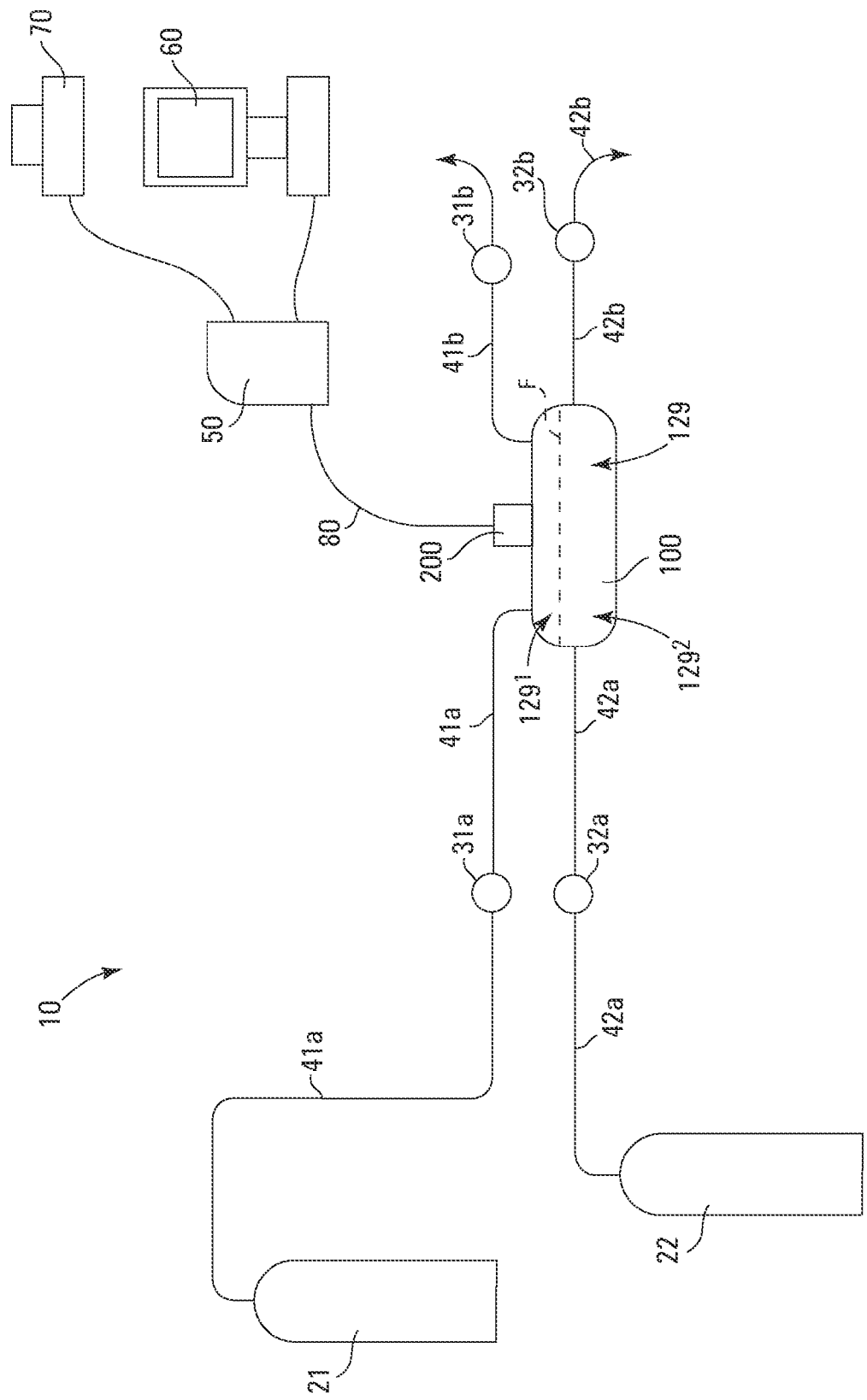
FIG. 1 is a schematic overview of one embodiment of a testing system useful for performing the testing process of the present invention.
Figure 2:
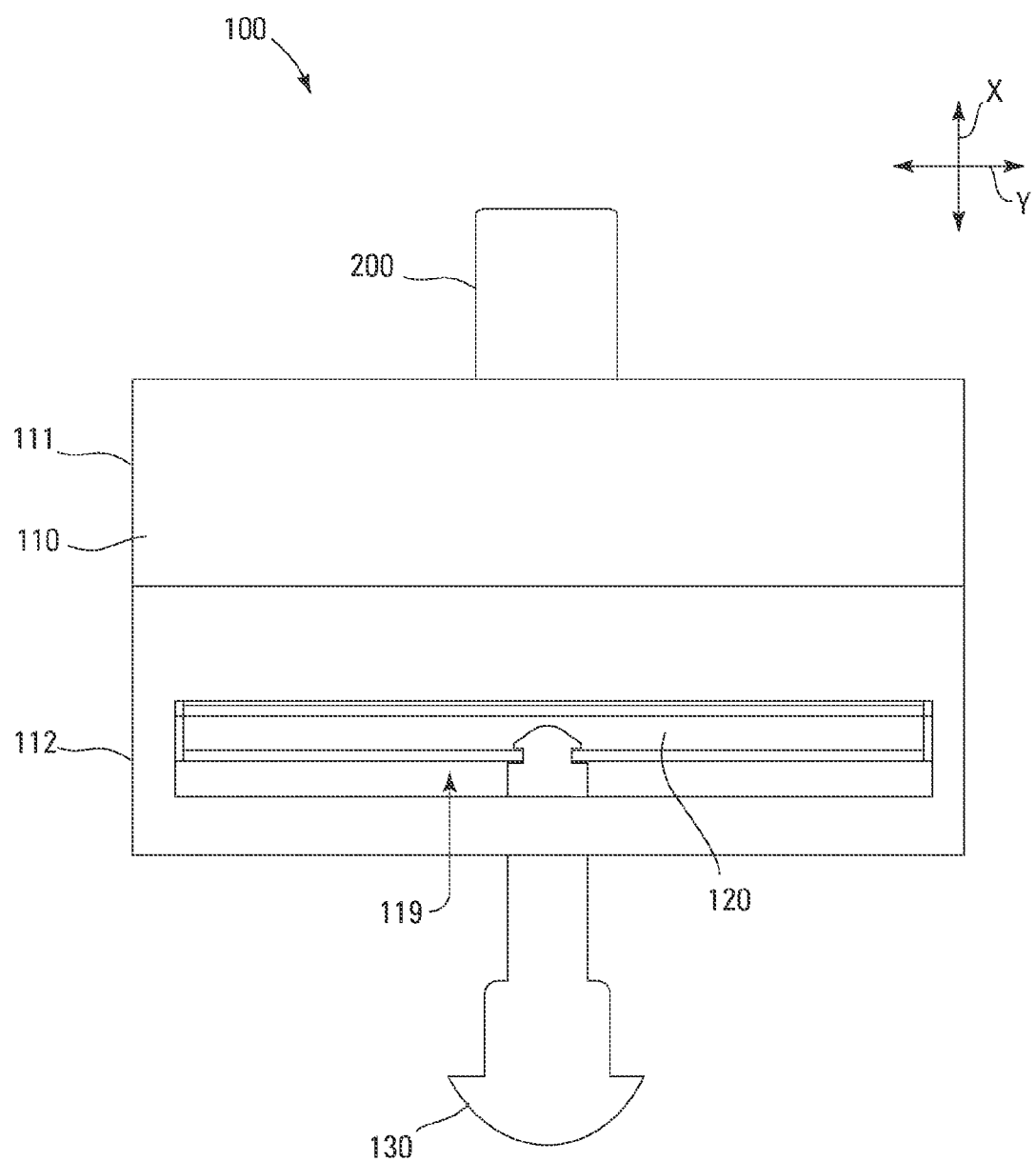
FIG. 2 is a side view of the measurement unit component of the testing system shown in FIG. 1.

Referring generally to FIG. 1, the invention is directed to a humidity control system 190 for an analyte permeation testing instrument 100. The system 190 includes (i) an analyte permeation testing instrument 100, (ii) a sensor 200 for sensing a target analyte A, (iii) a humidity control chamber 199, and (iv) a selectively permeable membrane 193 permeable to water vapor and impermeable to the target analyte A. The analyte permeation testing instrument 100 defines a testing chamber 129 operable for engaging a test film F such that the testing chamber 129 is sealingly separated by the test film F into a first cell 129$^1$ and a second cell 129$^2$ throughout a permeation testing period. The sensor 200 is placed in fluid communication with the first cell 129$^1$. The humidity control chamber 199 is placed in fluid communication with both a source of gas having a known humidity (not shown) and the first cell 129$^1$, with the selectively permeable membrane 193 sealingly separating the humidity control chamber 199 from the first cell 129$^1$.

By positioning the humidity control chamber 199 proximate to and in direct fluid communication with the first cell 129$^1$, through the selectively permeable membrane 193, the humidity control system 190 can quickly and effectively control the humidity within the first cell 129$^1$ even though the first cell 129$^1$ is sealed to fluid flow.

Specific Embodiment

Testing System

Construction

An exemplary embodiment of a testing system 10 capable of measuring the transmission rate of an analyte A through a film F in accordance with the present invention is depicted in FIG. 1. A measurement unit 100 defines a testing chamber 129 sealingly divided by a film F to be tested into an upper cell 129$^1$ and a lower cell 129$^2$. A source of an inert gas 21 communicates with the upper cell 129$^1$ via inlet conduit 41*a* and outlet conduit 41*b* for flushing the upper cell 129$^1$ prior to testing. Suitable inert gases include specifically, but not exclusively, nitrogen, argon, helium, krypton or a blend of nitrogen and hydrogen, etc. A source of test gas 22 containing a known concentration of an analyte A, communicates with the lower cell 129$^2$ via inlet conduit 42*a* and outlet conduit 42*b* for continuously providing the lower cell 129$^2$ with test gas to ensure that the concentration of analyte A within the lower cell 129$^2$ remains constant throughout a test period. Shutoff valves 31*a* and 31*b* are provided in inlet conduit 41*a* and outlet conduit 41*b* respectively, for controlling the flow of inert gas through the upper cell 129$^1$. Similarly, shutoff valves 32*a* and 32*b* are provided in inlet conduit 42*a* and outlet conduit 42*b* respectively, for controlling the flow of gas through the lower cell 129$^2$.

An analyte sensor 200 for the target analyte A is placed in fluid communication with the upper cell 129$^1$ for sensing the presence of target analyte A within the upper cell 129$^1$. Typical target analytes include oxygen, carbon dioxide, carbon monoxide and water vapor. The analyte sensor 200 may be selected from any of the wide variety of commercially available consuming sensors capable of detecting and consuming the target analyte A, with electrochemical sensors generally preferred based upon the high sensitivity and low cost of such sensors and the fact that such sensors, when employed in the present invention, follow Faraday's Law—eliminating the need to calibrate the sensor.

The analyte sensor 200 communicates via electrical leads 80 with a suitable central processing unit 50 equipped with electronic memory (not shown), and optionally but preferably attached to a monitor 60 and/or printer 70 for storing and reporting analyte A concentrations detected by the analyte sensor 200.

Use

A film F to be tested is "loaded" into the testing chamber 129 so as to sealingly separate the testing chamber 129 into an upper cell 129$^1$ and a lower cell 129$^2$ with a known area of the film F exposed to both cells 129$^1$ and 129$^2$. Shutoff valves 31*a* and 31*b* are then opened to permit the flow of inert gas through the upper cell 129$^1$ for flushing analyte A from the upper cell 129$^1$. After flushing, the shutoff valves 31*a* and 31*b* are closed to seal-off the upper cell 129$^1$ from the surrounding environment. Shutoff valves 32*a* and 32*b* are then opened to permit the flow of gas containing a known concentration of analyte A into the lower cell 129$^2$. The presence of analyte A within the upper cell 129$^1$ is then detected and recorded by the analyte sensor 200. By ensuring that the only route through which analyte A can enter into the upper cell 129$^1$ is through the "exposed" area of the film F, and by selecting an analyte sensor 200 that consumes analyte A faster than the analyte A is transmitted through the film F, then the rate at which the analyte sensor 200 detects analyte A, once a steady state rate is attained, can be equated directly to the analyte transmission rate for the known "exposed" area of the film F.

Measurement Unit

Construction

An exemplary embodiment of a measurement unit 100 capable of quickly and accurately measuring the transmission rate of an analyte A through a film F in accordance with the present invention is depicted in FIGS. 2-6.

The measurement unit 100 includes (i) a housing 110, (ii) mounting plates 120, (iii) an actuator 130, (iv) a valve 140 for controlling fluid communication with an analyte sensor 200, (v) channels 150 in the housing 110 and mounting plates 120 for directing test gas (not shown) into a lower cell 129$^2$ in the mounting plates 120, and (vi) a flow control system (not collectively numbered) including flow control channels 170 and o-ring seals 180 for selectively opening and sealing closing an upper cell 129$^1$ in the mounting plates 120 to fluid flow. The measurement unit 100 optionally, but preferably, also includes a humidity control system 190.

The housing 110 includes an upper section 111 and a lower section 112 that cooperatively define a retention chamber 119.

Referring to FIGS. 4A, 4B, 5A, 5B, 6A and 6B, upper and lower mounting plates 121 and 122 (collectively referenced as mounting plates 120) are retained within the retention chamber 119 defined by housing 110 with the upper surface 121*u* of the upper mounting plate 121 longitudinally y offset a distance from the lower surface 111*i* of the upper section 111 of the housing 110 so as to define a gap 160 therebetween. The upper and lower mounting plates 121 and 122 define a testing chamber 129 therebetween. An o-ring 125 encircling the testing chamber 129 is provided between the mounting plates 120. The testing chamber 129 can be sealingly divided into an upper cell 129$^1$ and a lower cell 129$^2$ by placement of a test film F between the mounting plates 120 overlaying the o-ring 125, and compressing the mounting plates 120 together so as to sealingly compress the entire periphery of the o-ring 125 between the mounting plates 120.

It is generally preferred to configure the testing chamber 129 to provide an upper cell 129$^1$ of about 1 cm$^3$ to about 3 cm$^3$. An upper cell 129$^1$ larger than about 3 cm$^3$ is too slow to respond as molecules of analyte A within the upper cell 129$^1$ can be consumed and detected by the analyte sensor 200 only when the molecules enter the analyte sensor 200 and the upper cell 129$^1$ relies solely upon diffusion to move molecules within the upper cell 129$^1$. An upper cell 129$^1$ smaller than about 1 cm$^3$ tends to cause areas of the film F to contact with the upper surface (not numbered) of the upper mounting plate 121 during the testing period, thereby introducing error into the test results as analyte A cannot readily pass through the film F into the upper cell 129$^1$ through these "covered" areas.

Figure 4B:
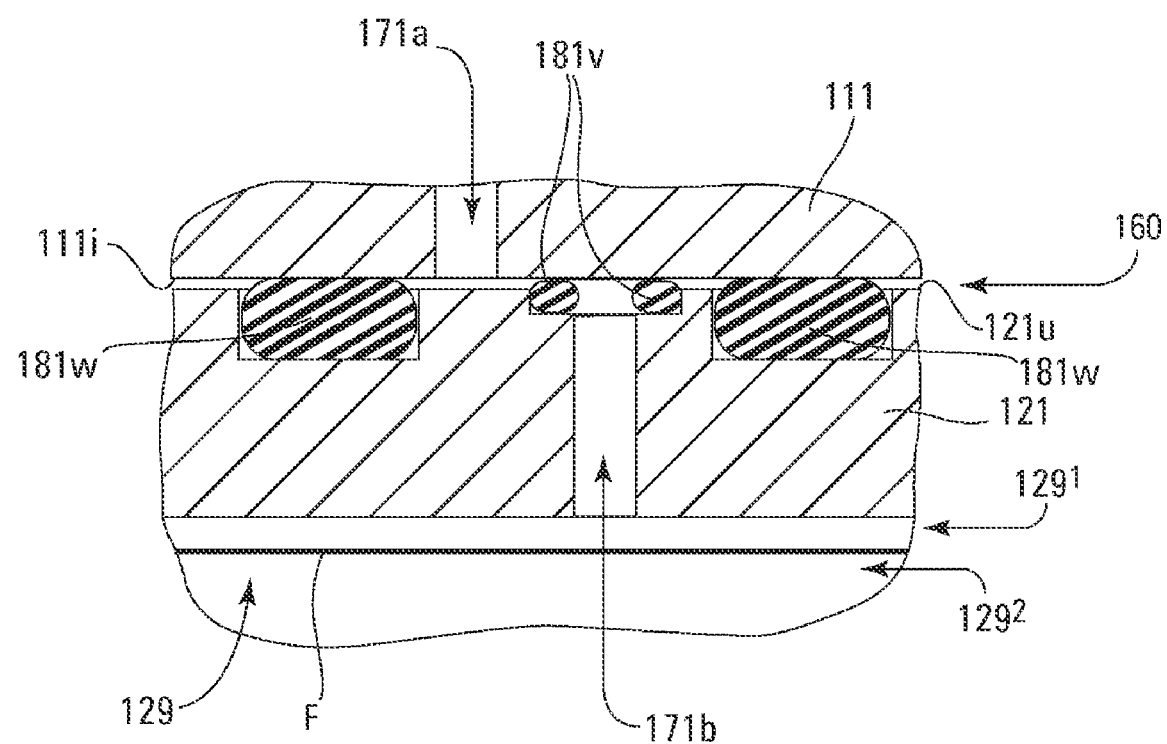

Referring to FIGS. 4A, 4B, 5A, 5B, 6A and 6B, the lower mounting plate 122 is mounted onto the distal end (unnumbered) of an actuator shaft 131 for longitudinally repositioning of the mounting plates 120 by an actuator 130 as between a lower or open position creating a longitudinally thicker gap 160 between the upper surface 121*u* of the upper mounting plate 121 and the lower surface 111*i* of the upper section 111 of the housing 110, as shown in FIG. 4 (collectively 4A, 4A$^1$, 4A$^2$ and 4A$^3$), and an upper or closed position creating a longitudinally thinner gap 160 between the upper surface 121*u* of the upper mounting plate 121 and the lower surface 111*i* of the upper section 111 of the housing 110, as shown in FIG. 5 (collectively 5A, 5A$^1$, 5A$^2$ and 5A$^3$).

Referring to FIGS. 6A and 6B, fluid flow into the lower cell 129$^2$ is provided by aligned inlet channels 151*a*, 151*b* and 151*c* in the upper section 111 of the housing 110, the upper mounting plate 121 and the lower mounting plate 122 respectively. In similar fashion, fluid flow out from the lower cell $129^2$ is provided by aligned outlet channels 152a, 152b and 152c in the upper section 111 of the housing 110, the upper mounting plate 121 and the lower mounting plate 122 respectively. A large diameter o-ring 151w is positioned within the gap 160 encircling the inlet channels 151a and 151b in the upper section 111 of the housing 110 and the upper mounting plate 121 for preventing testing gas from flowing throughout the gap 160. In similar fashion, a large diameter o-ring 152w is positioned within the gap 160 encircling the outlet channels 152a and 152b in the upper section 111 of the housing 110 and the upper mounting plate 121 for preventing testing gas from flowing throughout the gap 160.

Referring to FIGS. 4A and 4B, the flow control system (not collectively numbered) includes (i) flow control channels and passageways 170 through the upper section 111 of the housing 110 and the upper mounting plate 121, and (ii) o-ring seals 180 of different diameters and different thicknesses positioned within the gap 160 and encircling the various channels and passageways 170. The flow control system provides a quick, simple and reliable method of opening and closing the upper cell $129^1$ and the analyte sensor 200 to fluid flow at the appropriate times.

Referring to FIGS. 4A and $4A^1$, fluid flow into the upper cell $129^1$ is provided by laterally x and/or transversely z offset inlet channels 171a and 171b in the upper section 111 of the housing 110 and the upper mounting plate 121 respectively. In similar fashion, referring now to FIGS. 4A and $4A^2$, fluid flow out from the upper cell $129^1$ is provided by laterally x and/or transversely z offset outlet channels 172a and 172b in the upper section 111 of the housing 110 and the upper mounting plate 121 respectively.

Referring to FIGS. 4A and $4A^1$, a small diameter o-ring 181v is positioned within the gap 160 encircling the inlet channel 171b in the upper mounting plate 121. A large diameter o-ring 181w is also positioned within the gap 160 for encircling both the inlet channel 171a in the upper section 111 of the housing 110 and the inlet channel 171b in the upper mounting plate 121 as well as fully encircling the small diameter o-ring 181v. In similar fashion, referring now to FIGS. 4A and $4A^2$, a small diameter o-ring 182v is positioned within the gap 160 encircling the outlet channel 172b in the upper mounting plate 121, with a large diameter o-ring 182w positioned within the gap 160 and encircling both the outlet channel 172a in the upper section 111 of the housing 110 and the outlet channel 172b in the upper mounting plate 121 as well as encircling the small diameter o-ring 182v.

Referring to FIGS. 4A, $4A^1$, $4A^2$, $4A^3$, 5A, $5A^1$, $5A^2$ and $5A^3$, the thickness or longitudinal y height of the large diameter o-rings 181w and 182w is selected so that these o-rings 181w and 182w are sealingly engaged within the gap 160 regardless of whether the mounting plates 120 are in the open or closed longitudinally y position so as to prevent fluid from flowing freely within the gap 160. The thickness or longitudinal y height of the smaller diameter o-rings 181v and 182v is selected so that these o-rings 181v and 182v are sealingly engaged within the gap 160 only when the mounting plates 120 are in the closed longitudinally y position. Such positioning of the larger (181w and 182w) and smaller (181v and 182v) o-rings, in combination with the different thicknesses of the larger (181w and 182w) and smaller (181v and 182v) o-rings, permits the inlet (171a and 171b) and outlet (172a and 172b) channels to be simultaneously opened to fluid flow for flushing of the upper cell $129^1$ prior to a testing period by longitudinally y moving the mounting plates 120 into the downward or open position as shown in FIGS. 4A, $4A^1$ and $4A^2$, and simultaneously closed to fluid flow for sealing-off the upper cell $129^1$ during a testing period by longitudinally y moving the mounting plates 120 into the upward or closed position as shown in FIGS. 4B, $4B^1$ and $4B^2$.

Referring to FIGS. 4A, $4A^3$, 5A and $5A^3$, the analyte sensor 200 communicates with the upper cell $129^1$ via longitudinally y aligned passageways 173a and 173b in the upper section 111 of the housing 110 and the upper mounting plate 121 respectively. A large diameter o-ring 183w is positioned within the gap 160 encircling both passageways 173a and 173b for ensuring that fluid diffusing into the analyte sensor 200 from the upper cell $129^1$ is not contaminated by fluid from the gap 160.

In order to extend the useful life of the analyte sensor 200, especially when an electrochemical sensor is employed, the passageway 173a should be closed at all times except during testing periods (i.e., only after the upper cell $129^1$ has been flushed with an inert gas and sealed so that the only analyte A in the upper cell $129^1$ is analyte A that has permeated through a test film F). Referring to FIGS. 4A, $4A^3$, 5A and $5A^3$, an expedient technique for providing such limited access to the analyte sensor 200 is to position a normally closed tire valve 140 within the passageway 173a, with the body 141 of the tire valve 140 sealingly wedged into the passageway 173a and the stem 142 of the tire valve 140 extending longitudinally y downward towards the gap 160. An upwardly extending pin 121n is provided on the upper mounting plate 121 for pressing longitudinally y upward against the valve stem 142 and thereby opening the valve 140 only when the mounting plates 120 are in the upper or closed position.

The transmission rate of analyte A through most plastic films F is sensitive to humidity, with an increase in humidity tending to result in an increase in the transmission rate. Most analyte sensors 200 are also somewhat sensitive to humidity, especially if permitted to "dry out". Hence, in order to obtain consistent and comparable test results it is important to maintain a constant relative humidity within the testing chamber 129, especially within the closed upper cell $129^1$. To maintain a constant humidity within the upper cell $129^1$, a humidity control system 190 can be provided. A suitable humidity control system 190 is shown in FIGS. 5A, $5A^1$, 5B and $5B^1$. The humidity control system 190 include a pair of humidity control chambers 199 in the upper mounting plate 121 diametrically positioned relative to the analyte sensor 200 and in fluid communication with both the upper cell $129^1$ and the gap 160. Inlet 191a and outlet 192a channels are provided in the upper section 111 of the housing 110 for placing each of the humidity control chambers 199 in fluid communication with a source of a gas (not shown) having a known humidity, typically 0% or 100% relative humidity. A large diameter o-ring 198w is positioned within the gap 160 encircling each of the humidity control chambers 199 and the corresponding set of inlet 191a and outlet 192a channels. A film 193 permeable to water vapor and impermeable to the target analyte A, such as a Nafion® film, is provided over the opening of each humidity control chamber 199 into the upper cell $129^1$ for purposes of allowing transpiration between the humidity control chamber 199 and the upper cell $129^1$ without introducing extraneous analyte A into the upper cell $129^1$ or allowing analyte A to escape from the upper cell $129^1$ undetected. The selectively permeable film 193 can be sealingly held in position within each humidity control chamber 199 by an o-ring 194, washer 195, inset ring 196 and locking ring 197 as shown in FIGS. $5A^1$ and $5B^1$.

Use

The mounting plates 120 are removed from the retention chamber 129 by activating the actuator 130 to lower the actuator shaft 131 into a removal position (not shown) where the o-ring seals 180 within the gap 160 no longer contact the upper section 111 of the housing 110, and sliding the mounting plates 120 out through an open side (not numbered) of the lower section 112 of the housing 110.

The upper mounting plate 121 is then separated from the lower mounting plate 122, and a sample of the film F to be tested placed atop the lower mounting plate 122 over the test chamber 129 so as to fully engage the entire periphery of the o-ring 125 encircling the test chamber 129.

The upper mounting plate 121 is then placed back atop the lower mounting plate 122 and secured to the lower mounting plate 122 so as to sealingly clamp the film F between the plates 121 and 122, thereby sealingly separating the testing chamber 129 into an upper cell $129^1$ and a lower cell $129^2$ with a known area of the film F exposed to both cells $129^1$ and $129^2$. The "loaded" mounting plates 120 are then slid back into the retention chamber 119.

Referring to FIGS. 4A, $4A^1$, $4A^2$ and $4A^3$, the actuator 130 is activated to move the loaded mounting plates 120 into an "open" position wherein the larger diameter o-rings 181w, 182w, 183w and 198w located within the gap 160 sealingly engage the lower surface 111i of the upper section 111 of the housing 110 while the smaller diameter o-rings 181v and 182v within the gap 160 do not. With the mounting plates 120 in the "open" position, the upper cell $129^1$ is flushed with an inert gas to remove any target analyte A from the upper cell $129^1$ by placing the inlet channel 171a in the upper section 111 of the housing 110 in fluid communication with a pressurized source of inert gas 21 and allowing the inert gas to flow sequentially through the inlet channel 171a in the upper section 111 of the housing 110, through that portion of the gap 160 surrounded by the larger diameter o-ring 181w, through the inlet channel 171b in the upper mounting plate 121, through the upper cell $129^1$, through the outlet channel 172b in the upper mounting plate 121, through that portion of the gap 160 surrounded by the larger diameter o-ring 182w, and out from the measurement unit 100 through the outlet channel 172a in the upper section 111 of the housing 110.

Referring to FIGS. 4B, $4B^1$, $4B^2$ and $4B^3$, after flushing, the actuator 130 is activated to move the loaded mounting plates 120 into a "closed" position wherein both the larger diameter o-rings 181w, 182w, 183w and 198w and smaller diameter o-rings 181v and 182v within the gap 160 sealingly engage the lower surface 111i of the upper section 111 of the housing 110 so as to seal-off the upper cell $129^1$ from the surrounding environment.

Referring to FIG. $4A^3$, movement of the loaded mounting plates 120 into the "closed" position also causes the pin 121n on the upper mounting plate 121 to engage the stem 142 on the valve 140 within the passageway 173a in the upper section 111 of the housing 110 so as to open the passageway 173a and thereby place the analyte sensor 200 in fluid communication with the upper cell $129^1$.

With the mounting plates 120 in the "closed" position, the lower cell $129^2$ is flushed with a test gas containing a known concentration of target analyte A and continuously supplied with "fresh" test gas throughout the testing period to ensure that the concentration of target analyte A within the lower cell $129^1$ remains constant. Test gas is introduced into the lower cell $129^2$ by placing the inlet channel 151a in the upper section 111 of the housing 110 in fluid communication with a pressurized source of test gas 22 and allowing the test gas to flow sequentially through the inlet channel 151a in the upper section 111 of the housing 110, through that portion of the gap 160 surrounded by the larger diameter o-ring 151w, through the inlet channel 151b in the upper mounting plate 121, through the inlet channel 151c in the lower mounting plate 122, through the lower cell $129^2$, through the outlet channel 152c in the lower mounting plate 122, through the outlet channel 152b in the upper mounting plate 121, through that portion of the gap 160 surrounded by the larger diameter o-ring 152w, and out from the measurement unit 100 through the outlet channel 152a in the upper section 111 of the housing 110.

Target analyte A will permeate through the film F as the analyte A seeks to diffuse through the film F from a region of higher concentration (i.e., the lower cell $129^2$) to a region of lower concentration (i.e., the upper cell $129^1$). Since test gas continuously flows through the lower cell $129^2$ the concentration of target analyte A in the region of higher concentration remains constant throughout the relevant test period. Similarly, since the analyte sensor 200 consumes target analyte A within the upper cell $129^1$ faster that the target analyte A permeates through the film F, the concentration of target analyte A in the region of lower concentration also remains constant at essentially zero throughout the relevant test period.

Eventually, the system will reach a steady state condition where the rate at which analyte A is detected in the upper cell $129^1$ by the analyte sensor 200 and reported by the central processing unit 50 remains constant. This steady state rate equates directly to the permeation rate for the film F for the "exposed" area of the film.

EXAMPLES

Example 1

A 1.0 mil thick polyethylene terephthalate mylar film is placed between the mounting plates of the permeation testing system depicted in FIGS. 1-7 so as to provide a 50 cm$^2$ area of the film exposed to both the upper and lower cells. Permeation testing is conducted in accordance with ASTM D3985 employing the following testing parameters:

Gas In Upper Cell:
  Type: 100% N$_2$
  RH: 10%
Gas In Lower Cell:
  Type: 100% O$_2$
  RH: 10%
Testing Chamber Temp: 23° C.
Barometer: 742.3 mmHg Oxygen within the upper cell is continuously sensed with a high-sensitivity standard electrochemical oxygen sensor covered with a porous membrane. Utilizing a reporting cycle of five (5) minutes, the transmission rate of oxygen through the film (O2TR) is calculated from the amperes sensed by the sensor each reporting cycle utilizing EQUATION A. The O2TR calculated for each reporting cycle throughout the testing period is depicted in FIG. 8 and set forth in Table One below. The O2TR for the film, reported after fifty (50) reporting cycles (4 hours and 10 minutes) is 60.975 cm$^3$/(m$^2$)(day).

$$O2TR = Amperes/(Area)(k_1)(k_2)(k_3) \quad \text{(EQUATION A)}$$

Wherein:
O2TR=Transmission Rate of Oxygen (cm$^3$/(m$^2$)(sec))
Amperes=Amperes generated at the sensor (coulombs/second)
Area=Exposed area of the film (m$^2$)
$k_1$=Molecules of Oxygen per cm$^3$ at Standard Temperature and Pressure (2.6876*10$^{19}$ molecules/cm$^3$)
$k_2$=Electrons involved in covalent bonding @ the sensor per molecule of Oxygen (4 e$^-$/molecule)

$k_3$=Coulombs generated per electron ($1.6*10^{-19}$ coulombs/e-)

TABLE ONE

| Time (hrs:min) | O2TR $cm^3/(m^2)(day)$ |
|---|---|
| 5 | 0.1 |
| 10 | 5.078 |
| 15 | 15.105 |
| 20 | 25.023 |
| 25 | 33.235 |
| 30 | 39.666 |
| 35 | 47.96 |
| 40 | 51.218 |
| 45 | 53.614 |
| 50 | 55.399 |
| 55 | 56.72 |
| 1:00 | 57.732 |
| 1:05 | 58.499 |
| 1:10 | 59.073 |
| 1:15 | 59.491 |
| 1:20 | 59.844 |
| 1:25 | 60.086 |
| 1:30 | 60.254 |
| 1:35 | 60.397 |
| 1:40 | 60.51 |
| 1:45 | 60.592 |
| 1:50 | 60.67 |
| 1:55 | 60.715 |
| 2:00 | 60.769 |
| 2:05 | 60.785 |
| 2:10 | 60.807 |
| 2:15 | 60.84 |
| 2:20 | 60.857 |
| 2:25 | 60.843 |
| 2:30 | 60.858 |
| 2:35 | 60.858 |
| 2:40 | 60.896 |
| 2:45 | 60.9 |
| 2:50 | 60.935 |
| 2:55 | 60.952 |
| 3:00 | 60.957 |
| 3:05 | 60.973 |
| 3:10 | 60.97 |
| 3:15 | 60.966 |
| 3:20 | 60.954 |
| 3:25 | 60.959 |
| 3:30 | 60.948 |
| 3:35 | 60.98 |
| 3:40 | 60.984 |
| 3:45 | 60.978 |
| 3:50 | 60.974 |
| 3:55 | 60.973 |
| 4:00 | 60.984 |
| 4:05 | 60.968 |
| 4:10 | 60.975 |

We claim:

1. A humidity control system for an analyte permeation testing instrument, comprising:
    (a) an analyte permeation testing instrument defining a testing chamber operable for engaging a test film such that the testing chamber is sealingly separated by the test film into a first cell and a second cell throughout a permeation testing period,
    (b) a sensor for sensing a target analyte, wherein the sensor is in fluid communication with the first cell,
    (c) a humidity control chamber positioned adjacent the first cell and in fluid communication with a source of gas having a known humidity and the first cell, and
    (d) a selectively permeable membrane sealingly separating the humidity control chamber from the first cell, wherein the selectively permeable membrane is permeable to water vapor and impermeable to target analyte.

2. The humidity control system of claim 1 wherein the sensor is an oxygen sensor.

3. The humidity control system of claim 1 wherein the sensor is a carbon monoxide sensor.

4. The humidity control system of claim 1 wherein the sensor is a carbon dioxide sensor.

5. The humidity control system of claim 1 wherein the first cell is sealed to fluid flow throughout the entire duration of each permeation testing period.

6. The humidity control system of claim 1 wherein the known humidity is 0%.

7. The humidity control system of claim 1 wherein the known humidity is 100%.

8. The humidity control system of claim 1 wherein the known humidity is between 10% and 90%.

9. The humidity control system of claim 1 wherein the selectively permeable membrane is a sulfonated tetrafluoroethylene copolymer membrane.

10. The humidity control system of claim 9 wherein the selectively permeable membrane is a Nafion membrane.

11. The humidity control system of claim 1 further comprising inlet and outlet channels in fluid communication with the humidity control chamber for introducing and venting the gas having a known humidity into and out from the humidity control chamber.

12. The humidity control system of claim 1 wherein (i) an opening providing fluid access from the first cell to the sensor is centrally positioned within the first cell, and (ii) the system includes at least a pair of separate and independent humidity control chambers diametrically opposed about the opening from the first cell to the sensor with each humidity control chamber sealingly separated from the first cell by a selectively permeable membrane.

\* \* \* \* \*